(12) United States Patent
Almonacid et al.

(10) Patent No.: US 10,796,783 B2
(45) Date of Patent: Oct. 6, 2020

(54) METHOD AND SYSTEM FOR MULTIPLEX PRIMER DESIGN

(71) Applicant: PSOMAGEN, INC., Rockville, MD (US)

(72) Inventors: Daniel Almonacid, San Francisco, CA (US); Zachary Apte, San Francisco, CA (US); Jessica Richman, San Francisco, CA (US)

(73) Assignee: PSOMAGEN, INC., Rockville, MD (US)

( * ) Notice: Subject to any disclaimer, the term of this patent is extended or adjusted under 35 U.S.C. 154(b) by 389 days.

(21) Appl. No.: 15/240,919

(22) Filed: Aug. 18, 2016

(65) Prior Publication Data

US 2017/0053061 A1    Feb. 23, 2017

Related U.S. Application Data (60) Provisional application No. 62/206,654, filed on Aug. 18, 2015.

(51) Int. Cl.

| | | |
|---|---|---|
| G01N 33/48 | (2006.01) |
| G16B 25/00 | (2019.01) |
| C12Q 1/6844 | (2018.01) |
| G16B 30/00 | (2019.01) |
| G16B 35/00 | (2019.01) |
| G16C 20/60 | (2019.01) |
| C12Q 1/6806 | (2018.01) |
| G16C 99/00 | (2019.01) |
| G01N 35/00 | (2006.01) |

(52) U.S. Cl.
CPC .......... *G16B 25/00* (2019.02); *C12Q 1/6806* (2013.01); *C12Q 1/6844* (2013.01); *G16B 30/00* (2019.02); *G16B 35/00* (2019.02); *G16C 20/60* (2019.02); *G16C 99/00* (2019.02); *G01N 35/0099* (2013.01); *G01N 2035/00881* (2013.01)

(58) Field of Classification Search
None
See application file for complete search history.

(56) References Cited

U.S. PATENT DOCUMENTS

| | | | |
|---|---|---|---|
| 6,632,641 B1 | 10/2003 | Brennan et al. |
| 7,176,002 B2 | 2/2007 | Lao et al. |
| 9,149,473 B2 | 10/2015 | Ecker et al. |
| 2002/0012926 A1 | 1/2002 | Quake et al. |
| 2005/0196785 A1 | 9/2005 | Quake et al. |
| 2006/0073501 A1 | 4/2006 | Boom et al. |
| 2006/0281113 A1* | 12/2006 | Church .................. C12N 15/10 435/6.12 |
| 2007/0259337 A1 | 11/2007 | Hully et al. |
| 2010/0035232 A1 | 2/2010 | Ecker et al. |
| 2010/0093560 A1* | 4/2010 | Colbeck ............... C12N 15/102 506/9 |
| 2015/0213193 A1 | 7/2015 | Apte et al. |
| 2016/0110515 A1 | 4/2016 | Apte et al. |
| 2016/0224748 A1 | 8/2016 | Apte et al. |
| 2016/0224749 A1 | 8/2016 | Apte et al. |
| 2016/0228003 A1 | 8/2016 | Apte et al. |
| 2016/0230217 A1 | 8/2016 | Apte et al. |
| 2016/0232280 A1 | 8/2016 | Apte et al. |
| 2016/0232312 A1 | 8/2016 | Apte et al. |
| 2016/0232313 A1 | 8/2016 | Apte et al. |
| 2016/0232319 A1 | 8/2016 | Apte et al. |
| 2016/0259909 A1 | 9/2016 | Apte et al. |
| 2017/0002432 A1 | 1/2017 | Apte et al. |
| 2017/0024527 A1 | 1/2017 | Apte et al. |

FOREIGN PATENT DOCUMENTS

EP    2631240 A1    8/2013

* cited by examiner

*Primary Examiner* — Anna Skibinsky
(74) *Attorney, Agent, or Firm* — Lex IP Meister, PLLC (57) ABSTRACT

A method and system for selection of a primer set for a set of target sequences includes: identifying candidate fragments upon performance of a comparison operation with the set of target sequences; identifying a forward subset of unique forward candidates and a reverse subset of unique reverse candidates; reducing the forward subset and the reverse subset based on a filtering operation; performing an in silico search operation with the reduced forward subset and the reduced reverse subset; generating a set of candidate degenerate primers based on the in silico search operation and a base mismatch criterion; generating a reduced set of candidate degenerate primers upon filtering the set of candidate degenerate primers according to the set of primer criteria; and selecting forward primer subsets that amplify the set of target sequences and identifying a reverse primer subset for each of the forward primer subsets with an in silico PCR operation.

23 Claims, 6 Drawing Sheets

METHOD AND SYSTEM FOR MULTIPLEX PRIMER DESIGN

CROSS-REFERENCE TO RELATED APPLICATIONS

This application claims the benefit of U.S. Provisional Application Ser. No. 62/206,654 filed 18 Aug. 2015, which is incorporated in its entirety herein by this reference.

TECHNICAL FIELD

This invention relates generally to the field of molecular diagnostics and more specifically to a new and useful method and system for multiplex primer design in the field of molecular diagnostics.

BACKGROUND

Processes involving amplification, detection, and analysis of nucleic acid targets within a sample can be used for sample characterization and/or diagnostic testing in research or clinical environments. Amplification, detection, and analysis of multiple nucleic acid targets are thus particularly useful in characterizing multiple sample components and or enabling diagnostics associated with multiple targets (e.g., health condition biomarkers). Current methods and systems for multiplexed amplification, detection, sequencing, and/or analysis of multiple nucleic acid targets in a high throughput manner are, however, limited by the number of reactions that can be performed within a single system (e.g., process chamber), which is due, in part, to undesired interactions between process components (e.g., primers) associated with each target being processed. Furthermore, current methods of multiplex sample processing are time consuming, labor intensive, and can be prohibitively expensive to implement.

As such, there is a need in the field of molecular diagnostics for a new and useful method and system for multiplex primer design. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Method

Figure 1A:
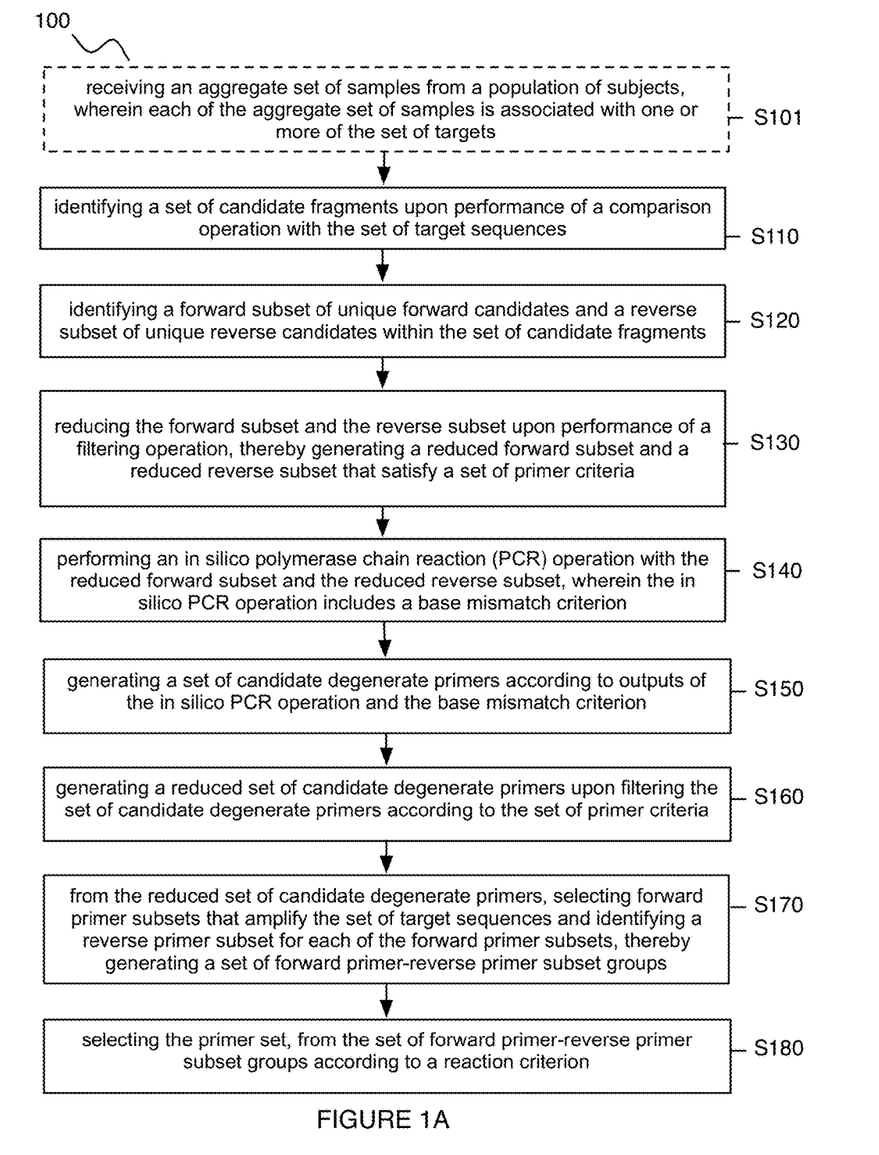
FIGS. 1A-1B are a schematics of an embodiment of a method for multiplex primer design.
Figure 1B:
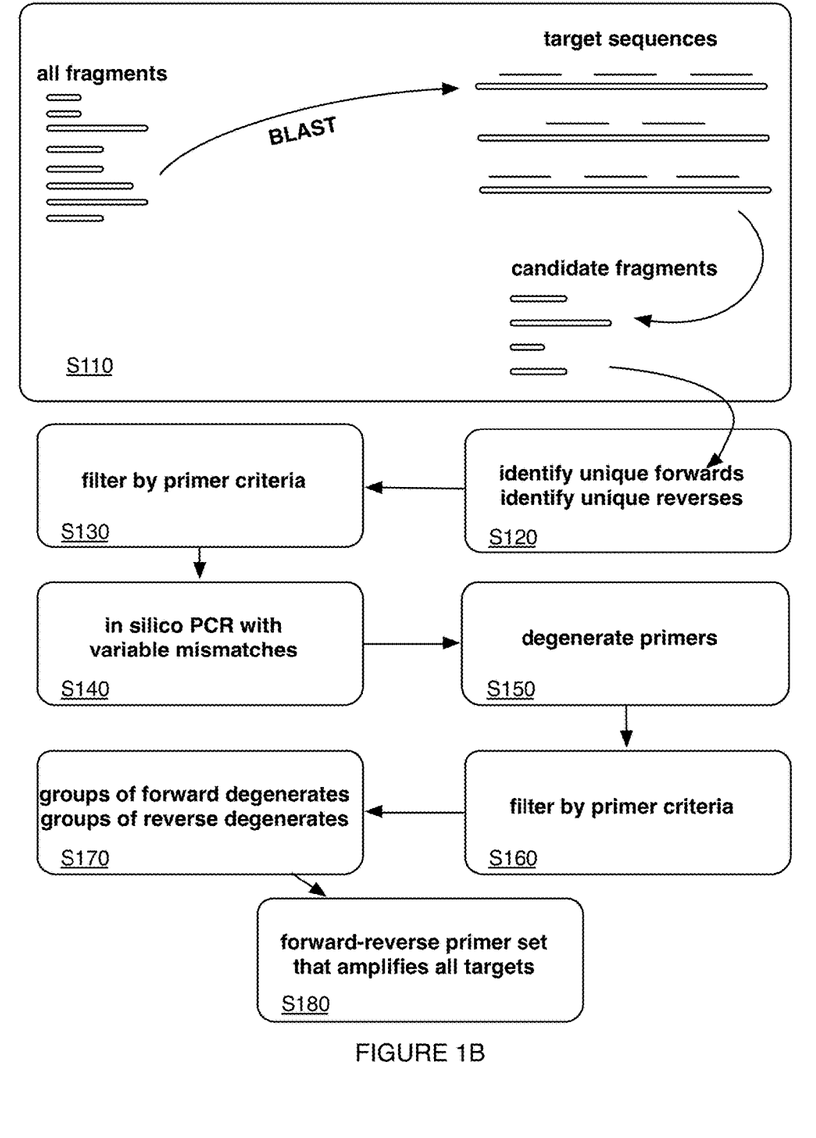

As shown in FIGS. 1A and 1B, an embodiment of a method 100 for selection of a primer set for amplification of a set of target sequences includes: identifying a set of candidate fragments upon performance of a comparison operation with the set of target sequences S110; identifying a forward subset of unique forward candidates and a reverse subset of unique reverse candidates within the set of candidate fragments S120; reducing the forward subset and the reverse subset upon performance of a filtering operation, thereby generating a reduced forward subset and a reduced reverse subset that satisfy a set of primer criteria S130; performing an in silico search operation with the reduced forward subset and the reduced reverse subset, wherein the in silico search operation includes a base mismatch criterion S140; generating a set of candidate degenerate primers according to outputs of the in silico search operation and the base mismatch criterion S150; generating a reduced set of candidate degenerate primers upon filtering the set of candidate degenerate primers according to the set of primer criteria S160; from the reduced set of candidate degenerate primers, selecting forward primer subsets that amplify the set of target sequences and identifying a reverse primer subset for each of the forward primer subsets with an in silico polymerase chain reaction (PCR) operation S170, thereby generating a set of forward primer-reverse primer subset groups; and selecting the primer set, from the set of forward primer-reverse primer subset groups according to a reaction criterion S180.

The method 100 functions to identify a set of forward primers and a matching set of reverse primers that amplify a set of targets simultaneously or contemporaneously, wherein the set of forward primers and the set of reverse primers are selected in a manner that prevents the occurrence of adverse primer-primer interactions, adverse primer interference effects, and/or any other adverse effects during use. As such, the method 100 can facilitate simultaneous performance of multiple experiments in a multiplexed manner, in increasing efficiency and reducing resource use associated with an experiment or assay. The method 100 can be implemented in clinical and/or research environments associated with molecular diagnostics. In specific examples, the method 100 can facilitate amplification, sequencing, detection, and analysis of targets associated with different health conditions or disease panels, microorganism ecology (e.g., microbiome composition), genomics, and any other suitable application wherein multiple target sequences need to be analyzed.

In various applications of the method 100, the set of primers selected can be used in polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique.

In particular, in implementation of the method(s) described, amplicons generated allow phylogenetic discrimination of the targets, such that analysis of the amplicons allows for discrimination of sample targets (e.g., bacteria, yeast, viruses), as described in more detail below.

The method 100 is preferably implemented at least in part at a computing system, wherein the computing system can be implemented in one or more of a computer, a workstation associated with an automated laboratory system, a semi-automated laboratory system, a remote server, a cloud-based computing system, a computing module of a mobile computing device, and any other suitable computing module. In some embodiments, the method 100 can be implemented by at least a portion of the embodiments, variations, and examples of the system described in U.S. application Ser. No. 14/593,424 entitled "Method and System for Microbiome Analysis" and filed on 9 Jan. 2015, and can facilitate embodiments, variations, and examples of the methods 100 described therein. However, the method 100 can additionally or alternatively be implemented using any other suitable system and/or facilitate implementation of any other suitable method, such as the system 200 described in Section 2 below.

1.1 Benefits

In specific examples, the method 100 and/or system 200 can confer several benefits over conventional methodologies for analyzing a sample of a subject in order to, for example, assess microbiome composition of samples from subjects, perform diagnostic testing (e.g., in relation to a respiratory condition panel, in relation to a sexually-transmitted disease panel, in relation to a vaginal flora panel, in relation to any other suitable panel), and/or otherwise assess composition of any other suitable sample in an efficient multiplexed manner. As such, the method 100 and/or system 200 can broadly be used to simultaneously amplify and/or analyze a set of nucleic acid targets in a reaction chamber with a designed set of primers. Conventional methodologies are inefficient, inconvenient, low throughput, low specificity, labor intensive, and/or possess other unsuitable characteristics for microbiome analysis. Thus, in specific examples, the method 100 and/or system 200 can perform one or more of the following:

First, the technology can facilitate analyses of a microbiome (and/or a human genome) of an individual in a multiplex manner, thereby enabling high throughput, comprehensive, specific diagnostic tests for a plurality of conditions, and/or general microbiome characterizations. For example, the technology can design primer sets configured to test for the presence of a panel of health conditions (e.g., as in a disease panel). Additionally or alternatively, a sample used in performing the diagnostic test can be contemporaneously analyzed for determining insights about microbiome, and used to provide generalized characterizations of the microbiome of a subject (e.g., in terms of composition and functional aspects). For example, primers can be algorithmically selected in relation to the amplification process for compatibility with a specific set of targets from which both diagnostic results and general microbiome insights can be generated. Thus, the technology can perform a comprehensive microbiome analysis to infer a variety of health indicators for an individual, thereby improving efficiency and the overall benefit extracted out of a given collected sample.

Second, the technology can enable a user to provide a single sample (e.g., at home, at work, remote from a health care provider, when the user is mobile, when the user is stationary, at any time of the day, etc.), and subsequently be digitally informed of both diagnostic results regarding his/her microbiome composition, a disease or a panel of diseases (e.g., an STD panel) as well as insights about their microbiome (e.g., health, composition, functionality, correlations with behavioral and/or demographic characteristics, etc.), using a testing platform that is capable of simultaneously identifying/assessing multiple target sequences using a set of specifically-designed primers. Additionally or alternatively, the sampling kit can facilitate a third party (e.g., a guardian, a care provider) and/or any suitable entity to collect a sample from the user. As such, the technology can be tailored for an optimal user experience through improvement of time investment, adherence, education, and treatment outcomes over conventional methodologies.

Third, the technology can generate and promote a therapy recommendation personalized for an individual based on their microbiome in a rapid and efficient manner, using a multiplexed sample processing methodology. Such therapy recommendations can include microbiome modification therapies (e.g., dietary supplementation with prebiotics/probiotics, physical activity recommendations, etc.), healthcare provider-related recommendations (e.g., suggestions to see a healthcare provider, facilitation of communication between user and physician), and/or any suitable (invasive or non-invasive) therapy recommendation tailored to an individual's microbiome make-up and situation, as further described below.

Fourth, a therapy recommendation and/or information derived from a microbiome can be accessible over any suitable device of the user (e.g., through a web portal associated with a user account, through a mobile application, etc.), thus enabling a seamless user experience from the beginning of the sample collection process to receiving the results inferred from the collected sample. Additionally or alternatively, the method 100 and/or system 200 can automatically implement a portion of the therapy recommendation (e.g., facilitating telemedicine, placing a probiotic supplementation order, notifying a health provider, etc.).

Fifth, the method can include automated generation of a designed set of primers (e.g., using a robotic system) from biomaterial components, in relation to automatically performing amplification reactions using the set of primers.

The technology can, however, provide any other suitable benefit(s) in the context of microbiome analysis, in the context of a panel of diseases (e.g., an STD panel), or in the context of any other suitable health-related state(s).

1.2 Method—Sample Reception

In some variations, the method 100 can include Block S101, which recites: receiving an aggregate set of samples from a population of subjects, wherein each of the aggregate set of samples is associated with one or more of the set of targets. Block S101 functions to acquire samples that can be processed with the primer set identified using other blocks of the method 100, in order to apply the results/outputs of the primer selection steps of the method 100 to real-world applications (e.g., in clinical/research environments). Block S101 can additionally or alternatively function to acquire samples that can be used to test efficacy of the outputs of the primer set selection process described below, in order to optimize or otherwise improve the method 100. In Block S101, the aggregate set of samples is preferably received from a wide variety of subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), and any other suitable trait that has an effect on microbiome composition, functional features and/or pharmacogenomics features. As such, as the number of subjects increases, the power of processes implemented in blocks of the method 100 increases, in relation to selecting appropriate primer sets that can be used to simultaneously amplify a set of targets.

In Block S101, sample reception can be implemented with system apparatus and in a manner described in the embodiments, variations, and examples of sample reception described in U.S. application Ser. No. 14/593,424 entitled "Method and System for Microbiome Analysis" and filed on 9 Jan. 2015, which is herein incorporated in its entirety by this reference. Furthermore, extensions of the method 100 described can additionally or alternatively implement embodiments, variations, and examples of sample processing described in U.S. application Ser. No. 14/593,424 entitled "Method and System for Microbiome Analysis" and filed on 9 Jan. 2015. The method 100 can, however, include any other suitable sample reception and/or processing steps.

1.3 Method—Candidate Fragments

Block S110 recites: identifying a set of candidate fragments upon performance of a comparison operation with the set of target sequences, which functions to reduce a large pool of candidate fragments to an isolated subset that could be used to amplify the set of target sequences. Block S110 is preferably implemented at a computing system specially configured to analyze a large pool of candidate fragments and compare features of those candidate fragments with features of the set of target sequences in order to perform a preliminary candidate reduction operation. As such, Block S110 is preferably implemented using a specialized computing system that is operable in a mode that performs the comparison operation of Block S110, as described in more detail in Section 2 below.

The comparison operation in Block S110 preferably comprises a sequence searching and comparison algorithm, and in a specific example can comprise using a variation of a Basic Local Alignment Search Tool (BLAST) to identify the set of candidate fragments. Variations of BLAST can include one or more of: a nucleotide-nucleotide BLAST (BLAST-N), a nucleotide 6-frame translation-nucleotide 6-frame translation (t-BLAST-x), a protein-nucleotide 6-frame translation (t-BLAST-n), a large numbers of query sequences BLAST (megaBLAST), a PowerBLAST operation, a Gapped BLAST operation, a PSI-BLAST operation, and any other suitable BLAST-associated operation. However, variations of Block S110 can additionally or alternatively include use of one or more of: a FASTA (e.g., FAST-N) sequence comparison tool; a BLAST-like alignment tool (BLAT), a KLAST operation, a PLAST operation, an ORIS tool, a VSEARCH tool, a USEARCH tool, and/or any other suitable tool for identifying the set of candidate fragments.

In relation to a BLAST operation used in Block S110, the BLAST operation can be performed with a set of BLAST parameters configured to facilitate identification of the set of candidate fragments in an efficient, focused, or otherwise desired manner. In variations of BLAST parameters, the set of BLAST parameters can include a gap open parameter, a gap extend parameter, a reward parameter, a penalty parameter, a percent identity parameter, a word size parameter, a dust parameter, a template length parameter, an ungapped extension parameter, a final gapped alignment parameter, a window size parameter, a filter parameter, and/or any other suitable BLAST parameter. In a specific example, the gap open parameter is set to 5, the gap extend parameter is set to 2, the reward parameter is set to 1, the penalty parameter is set to −4, and the word size is varied from ~18 to ~35, in association with a desired primer length. However, variations of the specific example of a set of BLAST parameters can include any other suitable values of the parameters.

In performing the comparison operation, Block S110 can thus include: at the computing system, identifying the set of candidate fragments, wherein the set of candidate fragments preferably have fragments of varying sizes (e.g., in terms of length, in terms of molecular weight, etc.) and/or fragments that are associated with different positions of one or more of the set of target sequences. As such, the set of candidate fragments preferably includes fragments of different sizes and/or different associated positions that can be used to determine optimized primer sets for amplifying all of the set of target sequences. In selecting candidate fragments, fragments can additionally or alternatively be chosen to target specific target sequences at multiple positions along a respective target sequence, in order to increase or decrease the number of amplicons associated with specific target sequences of the sample (which can help in downstream assembly steps associated with the method 100). For instance, the candidate fragments can be selected specifically for amplification of highly polymorphic sequences (e.g., at least one region from 16s rRNA sequences, from 18s rRNA sequences, from ITS sequences or from any other suitable sequence region).

Additionally or alternatively, Block S110 can include a k-mer approach, including: selecting a desired fragment length (e.g., 17-35 characters in length); fragmenting all targets into fragments of the desired length. In a specific example, a target of 1,000 bp can thus be chopped up into (1,000−20+1) fragments of size 20. Then, all the fragments that come from all targets can be compared in order to identify the most common one. In this approach, all possible fragments are explored exhaustively.

Block S110 thus preferably includes recording, in computing system memory, the sizes and the associated positions of the target sequence(s) corresponding to each of the set of candidate fragments, wherein the sizes and associated positions can be used as inputs in determining the ideal primer set according to subsequent blocks of the method 100. However, the set of candidate fragments identified in Block S110 can additionally or alternatively be substantially uniform in size (e.g., length, molecular weight, etc.) and/or uniform or different in any other suitable factor (e.g., position, melting temperature, binding energy, GC clamp, GC content, dinucleotide repeats, self dimer affinity, tendency to form hairpins, etc.).

1.4 Method—Candidate Fragment Reduction

Block S120 recites: identifying a forward subset of unique forward candidates and a reverse subset of unique reverse candidates within the set of candidate fragments, which functions to determine a first subset of forward candidates and a second subset of reverse candidates from the set of candidate fragments. Block S120 additionally functions to reduce the set of candidate fragments to a unique subset of fragments, which can increase efficiency (e.g., in terms of computational load) in subsequent blocks of the method 100 that process outputs of Block S120. Similar to Block S110, Block S120 is preferably implemented at a computing system specially configured to perform a specialized process during operation, wherein the operation can include an internal comparison operation to determine unique candidate fragments amongst the entire set of candidate fragments. As such, Block S120 is preferably implemented using a specialized computing system that is operable in a mode that performs one or more of the operations of Block S120, as described in more detail in Section 2 below.

In relation to uniqueness, the unique forward candidates identified in Block S120 can have similar positions (e.g., primer sequence positions) for binding to targets, in order to amplify a genome region that is similar for several primers. Furthermore, such a condition can allow one to make comparisons across the different amplicons generated using the set of primers. In a specific example, candidate primers (i.e., forward and reverse primers) for human papillomavirus (HPV) were configured to bind in a substantially restricted area of the HPV genome in order to obtain amplicons (e.g., ~750 bp amplicons) of the same gene for all HPVs tested.

Alternatively, the unique forward candidates identified in Block S120 can be unique in position (e.g., primer sequence position), such that Block S120 includes using the sequence positions associated with each fragment, as recorded in Block S110, to identify the forward fragments that are associated with a unique primer sequence position. In relation to uniqueness, Block S120 can additionally or alternatively include identifying and selecting forward candidates that are unique in size (e.g., length, molecular weight, etc.) and/or in any other suitable manner. Uniqueness (e.g., in position, in size, etc.) can thus be used as a factor in filtering candidate forward primers, indexing candidate forward primers, and/or otherwise prioritizing candidate forward primers in subsequent blocks of the method 100. Furthermore, variations of the method 100 can include using analyses of primer sequence similarity across a primer set to reduce the primer set to a reduced set of primers that are expected to anneal with mismatches to their target sequences or else degenerate primers.

Similarly, in relation to uniqueness of reverse candidates, the unique reverse candidates identified in Block S120 are preferably unique in position (e.g., primer sequence position), such that Block S120 includes using the sequence positions associated with each fragment, as recorded in Block S110, to identify the reverse fragments that are associated with a unique primer sequence position. In relation to uniqueness, Block S120 can additionally or alternatively include identifying and selecting reverse candidates that are unique in size (e.g., length, molecular weight, etc.) and/or in any other suitable manner. Uniqueness (e.g., in position, in size, etc.) can thus be used as a factor in filtering candidate reverse primers, indexing candidate reverse primers, and/or otherwise prioritizing candidate reverse primers in subsequent blocks of the method 100.

Block S130 recites: reducing the forward subset and the reverse subset upon performance of a filtering operation, thereby generating a reduced forward subset and a reduced reverse subset that satisfy a set of primer criteria. Block S130 functions to rank, index, or otherwise sort the forward subset and the reverse subset according to a set of criteria associated with reaction performance, prior to the in silico search operation performed in Block S140. Similar to Blocks S110 and S120, Block S130 is preferably implemented at a computing system specially configured to perform a specialized process during operation, wherein the operation can include a filtering operation to determine candidate fragments amongst the unique set of candidate fragments that satisfy a set of primer criteria of interest. As such, Block S130 is preferably implemented using a specialized computing system that is operable in a mode that performs one or more of the operations of Block S130, as described in more detail in Section 2 below.

In some variations, Block S130 can additionally include entirely removing one or more forward candidates and/or reverse candidates of the forward subset and the reverse subset from consideration in subsequent blocks of the method 100, based upon the set of primer criteria used in Block S130. However, some variations of Block S130 can include intermediately filtering one or more forward candidates and/or reverse candidates of the forward subset and the reverse subset from consideration at one stage of candidate filtering, but then reconsidering those preliminarily filtered candidates at a subsequent stage of candidate filtering.

In variations, the set of primer criteria used in Block S130 can include one or more of: a melting temperature criterion (e.g., related to thermocycling temperature limits of a reaction), an annealing temperature criterion, a binding energy criterion, a binding efficiency criterion, a GC clamp criterion associated with specific binding at the 3' end of a primer, a GC content criterion associated with a percentage of nitrogenous bases of a sequence, a run criterion (i.e. repeat criterion), an electrophoretic mobility criterion, a cross homology criterion, a specificity criterion, an internal stability criterion (e.g., a 3' end stability criterion, a 5' end stability criterion, a stability criterion associated with any position along the primer, etc.), a dinucleotide repeat criterion (i.e., a tandem repeat criterion), a self dimer formation criterion, a hairpin formation criterion, a secondary structure-related criterion, a complementarity criterion, a primer length criterion, and any other suitable criterion. Each of the criteria used in Block S130 can be weighted equally, or can alternatively be associated with different weights, in ranking or indexing the forward subset and the reverse subset of candidates. As such, ranking each of the set of candidates remaining during Block S130 can include implementing expression [1], where $C_i$ is the value of primer criterion i, $w_i$ is a weight associated with primer criterion i, and $f$ is a function of primer criteria and weights, where the function $f$ can include any one or more of: a multiplication operation, a division operation, an addition operation, a subtraction operation, and any other suitable operation:

$$\text{Candidate Ranking} = \Sigma f(C_i, w_i) \quad [1]$$

As such, in one specific example, a candidate can be ranked higher due to satisfaction of a melting temperature criterion (that is weighted more highly within the set of criteria), even though the candidate satisfies a GC content criterion (that is weighted less highly within the set of criteria) less satisfactorily. In another specific example, a candidate can be ranked lower due to satisfaction of a binding efficiency criterion (that is weighted extremely highly) less satisfactorily, even though the candidate satisfies other criteria (e.g., melting temperature criterion, GC content criterion, run criterion, repeat criterion) satisfactorily.

In relation to forward and/or reverse candidates that are not unique in other aspects not focused on in Block S120 (e.g., in terms of size, in terms of primer sequence position), Block S130 can additionally or alternatively include specifically filtering, ranking, indexing, or otherwise sorting multiple candidates according to one or more of the criteria described above.

As such, the set of primer criteria are configured to rank the forward subset and the reverse subset of candidates according to criteria associated with factors that facilitate prevention of adverse primer self interactions during a reaction (e.g., due to affinity to forming self dimers), prevent use of undesired primer morphologies (e.g., hairpins, GC clamps, other undesired structures, etc.) that can reduce reaction efficiency, identify candidates with potential ability to amplify multiple target sequences within the same reaction (e.g., with induced degeneracy), and otherwise improve primer performance during reaction. In relation to criteria associated with formation of primer secondary structures, Block S130 can include processing a candidate of Block S130 with one or more structure prediction tools, including one or more of: a OligoAnalyzer tool, a UNAFold Tool, a Benchling tool, a FastPCR software tool and any other suitable tool associated with primer design structure.

After indexing/ranking is performed with the filtering operation of Block S130, Block S130 can further include implementing a threshold condition to output the reduced forward subset and the reduced reverse subset for use in the in silico PCR operation of Block S140. The threshold condition can be directly associated with the ranks of the candidates (e.g., the top 500 forward candidates and the top 500 reverse candidates are passed to Block S140), or can additionally or alternatively be associated with any other suitable condition.

Block S130 can, however, include generating the reduced forward subset and the reduced reverse subset with any other suitable filtering operation and/or any other suitable set of criteria.

1.5 Method—In Silico Search Operation

Block S140 recites: performing an in silico search operation with the reduced forward subset and the reduced reverse subset, wherein the in silico search operation includes a base mismatch criterion. Block S140 functions to perform an expression search of each of the reduced forward subset and the reduced reverse subset against the set of target sequences, with allowance of mismatches in the search, thereby enabling a set of "compatible" primers to be identified according to the mismatch criterion. Similar to Blocks S110-S130, Block S140 is preferably implemented at a computing system specially configured to perform a specialized process during operation, wherein the operation can include an in silico search operation with a base mismatch allowance factor. As such, Block S140 is preferably implemented using a specialized computing system that is operable in a mode that performs one or more of the operations of Block S140, as described in more detail in Section 2 below.

The base mismatch criterion in Block S140 is preferably used to guide the level of degeneracy in the set of candidate degenerate primers generated in Block S150, which affects specificity of binding and/or other reaction characteristics. In Block S150, implementing the base mismatch criterion can including adjusting one or more base mismatch factors, wherein the factors can include one or more of: the number of base mismatches, the raw position of each mismatch, the position of each mismatch relative to other mismatches (e.g., in situations where multiple base mismatches are allowed), the position of each mismatch relative to a polymorphic region of a target sequence, and/or any other suitable base mismatch factor. In a specific example, the base mismatch criterion includes a criterion of 2-3 mismatches per forward primer and a criterion of 2-3 mismatches per reverse primer. Furthermore, in relation to the specific example, the positions of the mismatches can be varied for one or more primers and/or for one or more instances of the in silico search operation performed in Block S140.

Additionally or alternatively, the types and/or number of mismatches for each sequence of the reduced forward subset and the reduced reverse subset can be varied, such that the mismatches are not all identical. As such, a mismatch at a first position can be a mismatch in one or more of the bases A, C, G, or T, and a mismatch at a second position can be a mismatch in a different or the same base. As such, the type(s) of mismatches at multiple positions of a sequence of the reduced forward subset and the reduced reverse subset can be identical or different. The base mismatch criterion implemented in Block S140 can, however, be varied in any other suitable manner, according to requirements of a given experiment.

In variations, implementing the in silico search operation of Block S140 can include implementing a tool governed by one or more of an efficiency goal and a selectivity goal. In specific examples, Block S140 can implement one or more of: a digital polymerase chain reaction (dPCR) tool carried out using nucleic acid sequences an primer pair sequences in software, a virtual polymerase chain reaction (vPCR) tool carried out using nucleic acid sequences an primer pair sequences in software, and an electronic polymerase chain reaction (ePCR) tool carried out using nucleic acid sequences an primer pair sequences in software. In specific examples, implementing the in silico search operation of Block S140 can include implementing one or more of the following tools: PrimerAnalyser, PrimersList, PCR reaction setup calculators, universal dilution calculator, csPCR, Web-PCR, ePCR (accessible from the National Center for Biotechnology Information, at www.ncbi.nlm.nih.gov), Fast-PCR and any other suitable specific tool. For instance, a custom tool can take inputs comprising: a database of sequences, forward and reverse primers (e.g., individual primers or sets), and processing the inputs with a mismatch criterion, (e.g., set to 2-3 mismatches).

Additionally or alternatively, implementing the in silico search operation of Block S140 can include implementing a BLAST-based tool or any other suitable tool.

1.6 Method—Degenerate Primers

Block S150 recites: generating a set of candidate degenerate primers according to outputs of the in silico search operation and the base mismatch criterion, which functions to strategically select a group of degenerate primers, each degenerate primer able to bind to and amplify multiple target sequences of the set of target sequences. Similar to Blocks S110-S140, Block S150 is preferably implemented at a computing system specially configured to perform a specialized process during operation, wherein the operation transforms outputs of Block S140 into a set of proposed candidate degenerate primers that can ultimately cooperate to amplify the set of targets of a sample in a multiplexed manner. As such, Block S150 is preferably implemented using a specialized computing system that is operable in a mode that performs one or more of the operations of Block S160, as described in more detail in Section 2 below.

Block S150 thus initiates a portion of the method 100 that can identify different sets of forward degenerate primers and reverse degenerate primers for amplifying all target sequences in the set of target sequences. Block S150 preferably comprises using the results of the in silico search operation of Block S140 to identify the sequence mismatch configurations (e.g., type of degeneracy at a position, mismatch positions, and number of mismatches) that are conducive to generation of degenerate primers that amplify all of the target sequences. As such, generating each degenerate primer of the set of candidate degenerate primers in Block S150 can comprise grouping sequences of the same length that have different bases at the same position (e.g., as mismatches), if such mismatches produced favorable in silico PCR results in Block S140.

In more detail, Block S150 can include locating all matches outputted by the in silico search operation, wherein the matches each have specified distance (e.g., Hamming distance) from the original primers that the in silico search operation of Block S140 was performed with. Additionally or alternatively, any other suitable distance threshold (e.g., Damerau-Levenshtein distance threshold, Euclidean distance threshold, Mahalanobis distance threshold, Jaccard distance threshold, Sorensen similarity index threshold, etc.) that compares the difference between strings can be implemented in Block S150. As such, Block S150 can identify all degenerate primers that have a threshold distance/difference from an initial primer that the in silico search operation of Block S140 was conducted with.

After each match is identified, various methods, including an entropy-based method, can be used in Block S150 to identify the best degenerate primers that represent variations of primers identified in the in silico search operation of Block S140.

For each degenerate primer generated in Block S150, degeneracy can be in one or more positions of a sequence, and the type of degeneracy at a position can be identical to or different from the type of degeneracy at another position. Thus, degeneracy can be varied based upon application of use. As such, for one or more positions of a sequence, degeneracy at a position can be in: base A or G (i.e., given an R code); base C or T (i.e., given a Y code); base A or C (i.e., given an M code); base G or T (i.e., given a K code); base C or G (i.e., given an S code); base A or T (i.e., given a W code); base A, C, or T (i.e., given an H code); base C, G, or T (i.e., given a B code); base A, C, or G (i.e., given a V code); base A, G, or T (i.e., given a D code); or base A, C, G, or T (i.e., given a N code), according to IUPAC nomenclature. Furthermore, the type of degeneracy at the position(s) of a sequence of a degenerate primer can be designed according to an analysis of the number of target sequences that the degenerate primer can amplify, and/or any other suitable factor.

Block S150 can comprise generating degenerate primers in a pairwise manner, wherein degeneracy in a forward primer configured to amplify a subset of target sequences is used to design a corresponding degenerate reverse primer for amplification of the same subset of target sequences. In one such variation, Block S150 can include using degeneracy in a set of positions in a forward primer to design a reverse primer having degeneracy in the same positions as in the forward primer. In another such variation, Block S150 can include using degeneracy in a set of positions in a reverse primer to design a forward primer having degeneracy in the same positions as in the reverse primer. As such, degeneracy in a reverse primer configured to amplify a subset of target sequences can be used in Block S150 to design a corresponding degenerate forward primer for amplification of the same subset of target sequences. However, generation of the set of candidate degenerate primers in Block S150 in a pairwise manner can additionally or alternatively be performed in any other suitable manner.

1.7 Method—Filtering the Set of Candidate Degenerate Primers

Block S160 recites: generating a reduced set of candidate degenerate primers upon filtering the set of candidate degenerate primers according to the set of primer criteria, which, in a manner similar to Block S130, functions to rank, index, or otherwise sort the set of candidate degenerate primers according to a set of criteria associated with reaction performance. Similar to Blocks S110-S150, Block S160 is preferably implemented at a computing system specially configured to perform a specialized process during operation, wherein the operation can include a filtering operation to determine candidate degenerate primers from prior blocks of the method 100. As such, Block S160 is preferably implemented using a specialized computing system that is operable in a mode that performs one or more of the operations of Block S160, as described in more detail in Section 2 below.

In some variations, Block S160 can additionally include entirely removing one or more of the set of candidate degenerate primers from consideration in subsequent blocks of the method 100, based upon the set of primer criteria. As such, Block S160 can additionally facilitate efficiency (e.g., in terms of computational speed, computational load, in terms of improving performance of the computing system implementing portions of the method, etc.) of subsequent Blocks of the method 100, by removing some candidate degenerate primers from consideration.

The set of primer criteria used in Block S160 can include criteria identical to one or more criteria of the set of primer criteria used in Block S130, or can additionally or alternatively include criteria that are different from the set of primer criteria used in Block S130. As such, the set of primer criteria can include one or more of: a melting temperature criterion (e.g., related to thermocycling temperature limits of a reaction), an annealing temperature criterion, a binding energy criterion, a binding efficiency criterion, a GC clamp criterion associated with specific binding at the 3' end of a primer, a GC content criterion associated with a percentage of nitrogenous bases of a sequence, a run criterion (i.e. repeat criterion), an electrophoretic mobility criterion, a cross homology criterion, a specificity criterion, an internal stability criterion (e.g., a 3' end stability criterion, a 5' end stability criterion, a stability criterion associated with any position along the primer, etc.), a dinucleotide repeat criterion (i.e., a tandem repeat criterion), a self dimer formation criterion, a hairpin formation criterion, a secondary structure-related criterion, a complementarity criterion, a primer length criterion, and any other suitable criterion. Similar to Block S130, each of the criteria used in Block S160 can be weighted equally, or can alternatively be associated with different weights, in ranking or indexing the forward subset and the reverse subset of candidates. As such, ranking each of the set of candidate degenerate primers remaining during Block S160 can include implementing expression [2], where $c_i$ is a value of primer criterion i, $W_i$ is a weight associated with primer criterion i, and $f$ is a function of primer criteria and weights, where the function $f$ can include any one or more of: a multiplication operation, a division operation, an addition operation, a subtraction operation, and any other suitable operation:

$$\text{Candidate Ranking} = \Sigma f(c_i, W_i) \qquad [2]$$

As such, in one specific example, a candidate degenerate primer can be ranked higher due to satisfaction of a melting temperature criterion (that is weighted more highly within the set of criteria), even though the candidate degenerate primer satisfies a GC content criterion (that is weighted less highly within the set of criteria) less satisfactorily. In another specific example, a candidate degenerate primer can be ranked lower due to satisfaction of a binding efficiency criterion (that is weighted extremely highly) less satisfactorily, even though the candidate degenerate primer satisfies other criteria (e.g., melting temperature criterion, GC content criterion, run criterion, repeat criterion) satisfactorily.

As such, Block S160 can be used to rank the set of candidate degenerate primers according to criteria associated with factors that facilitate prevention of adverse primer self interactions during a reaction (e.g., due to affinity to forming self dimers), prevent use of undesired primer morphologies (e.g., hairpins, GC clamps, etc.) that can reduce reaction efficiency, identify candidates with potential ability to amplify multiple target sequences within the same reaction (e.g., with induced degeneracy), and otherwise improve primer performance during reaction. After indexing/ranking is performed with the filtering operation, a threshold condition can be used in Block S160 to output the reduced set of candidate degenerate primers for forward degenerate primer selection and reverse degenerate primer selection in Blocks S170 and S180. The threshold condition can be directly associated the ranks of the candidates (e.g., the top 100 forward degenerate candidates and the top 100 reverse degenerate candidates are passed to Block S170), or can additionally or alternatively be associated with any other suitable condition.

Block S160 can, however, include generating the reduced set of candidate degenerate primers with any other suitable filtering operation and/or any other suitable set of criteria.

1.8 Method—Selecting Primer Subsets

Block S170 recites: from the reduced set of candidate degenerate primers, selecting forward primer subsets that amplify the set of target sequences and identifying a reverse primer subset for each of the forward primer subsets with an in silico polymerase chain reaction (PCR) operation. Block S170 functions to find different combinations of forward degenerate primers from the reduced set of candidate degenerate primers outputted by Block S160 that amplify all of the set of targets, and corresponding combinations of reverse degenerate primers from the reduced set of candidate degenerate primers, thereby generating a set of forward primer-reverse primer subset groups. Similar to Blocks S110-S160, Block S170 is preferably implemented at a computing system specially configured to perform a specialized process during operation, wherein the operation includes an in silico PCR operation. As such, Block S170 is preferably implemented using a specialized computing system that is operable in a mode that performs one or more of the operations of Block S170, as described in more detail in Section 2 below.

Block S170 thus preferably comprises identifying groups of forward degenerate primers that can amplify all of the set of target sequences, wherein the number of forward primers is less than the number of target sequences. However, variations of Block S170 can include identifying groups of forward degenerate primers that can amplify all of the set of target sequences, wherein the number of forward primers is equal to or greater than the number of target sequences. In variations, the groups of forward degenerate primers can comprise overlapping forward degenerate primers, such that one or more forward degenerate primers are included in multiple groups. However, the groups of forward degenerate primers can alternatively be mutually exclusive.

Figure 2:
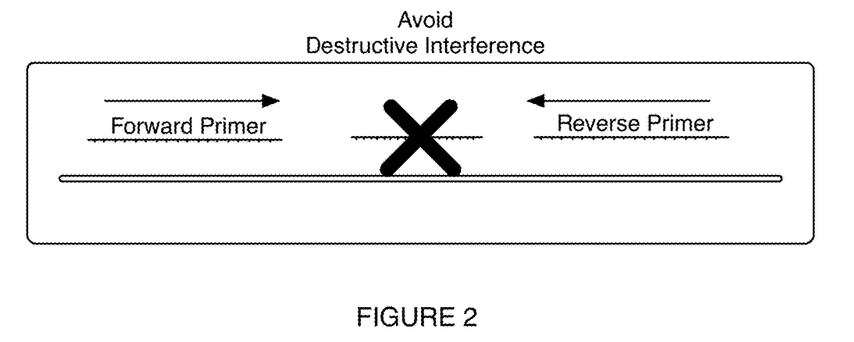
FIG. 2 depicts an example of a criterion associated with a portion of an embodiment of a method for multiplex primer design.

Once the groups of forward degenerate primers are identified, Block S170 comprises identifying corresponding groups of reverse degenerate primers, wherein the groups of reverse degenerate primers are preferably selected according to a set of constraints. In variations, the set of constraints can comprise a non-destructive interference constraint, an example of which is shown in FIG. 2, such that primers in either of the group of forward degenerate primers and the group of reverse degenerate primers are not liable to interfering with amplification processes of other primers. The set of constraints can, however, include any other suitable interference-related constraint, any other suitable dimer-related constraint, and/or any other suitable constraints or boundary conditions.

Block S170 can thus include performing an in silico PCR operation, which functions to implement computational tools to generate simulated (e.g., theoretical) PCR results from the reduced set of candidate degenerate primers outputted by Block S160. Block S170 can include implementing the in silico PCR operation using a custom in silico PCR application, using ePCR (accessible from the National Center for Biotechnology Information, at www.ncbi.nlm.nih-.gov), using FastPCR, using PrimerAnalyser, using PrimersList, using PCR reaction setup calculators, using a universal dilution calculator, using csPCR, using WebPCR, and using any other suitable specific tool or any other suitable software application for generating in silico PCR results.

As such, outputs of Block S170, in relation to simulated PCR results, can include one or more of: selectivity of primers used in the simulation, orientation of primers used in the simulation, length of amplicons generated with the primers used in the simulation, presence or absence of undesired amplicons generated in the simulation, simulation of electrophoretic mobility, and any other suitable data associated with design of appropriate short or long primer pairs for amplifying the set of target sequences. In particular, Block S170 preferably includes recording the associated positions, sequences, and lengths of the candidate forward and reverse primers used in the in silico PCR operation, as well as the simulated results of their use.

Block S170 can comprise performing the in silico PCR operation(s) in multiple stages, wherein different combinations of primers of the reduced forward subset and the reduced reverse subset are tested with the in silico PCR operation, and/or different combinations of target sequences for amplification are tested with the in silico PCR operation. Thus, for each instance of the in silico PCR operation performed in Block S170, different combinations of one or more of: sequence lengths, different levels of sequence mismatches, different abundances of forward primers and reverse primers, different relative abundances of forward primers and reverse primers, different reaction environment conditions (e.g., thermocycling conditions, annealing time, etc.) and any other suitable variable can be manipulated to identify and/or rank effective combinations of primers of the reduced forward subset and the reduced reverse subset.

In another variation, however, an identification of primers that could destructively interfere with each other can be used to generate protocols wherein the interfering primers can be applied in a manner that prevents destructive interference. In one such example, a protocol can involve application of interfering primers in stages, and in another example, a protocol can include use of interfering primers bound to substrates that prevent cross-interactions between primers, as described in U.S. application Ser. No. 14/593,424 entitled "Method and System for Microbiome Analysis" and filed on 9 Jan. 2015 and U.S. application Ser. No. 15/198,818 entitled "Method and System for Diagnostic Testing" and filed on 30 Jun. 2016, which are each incorporated in their entireties by this reference.

Figure 3:
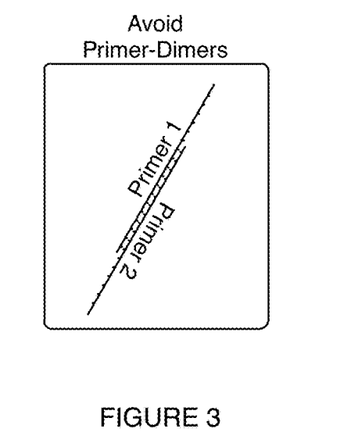
FIG. 3 depicts an example of a criterion associated with a portion of an embodiment of a method for multiplex primer design.

The set of constraints of Block S170 can additionally or alternatively include a constraint associated with a lack of tendency to form primer dimers (e.g., dimers with other primers), an example of which is shown in FIG. 3, and/or a lack of tendency to interfere and produce shortened amplicon products. Thus, in choosing a group of forward degenerate primers that is compatible with a corresponding group of reverse degenerate primers, the groups are preferably selected to avoid inclusion of primers that have beyond a threshold of likelihood to adversely interact (e.g., in forming self primer-dimers, in forming non-self primer-dimers, etc.) during a reaction.

In a specific example, processing the reduced set of candidate degenerate primers in Block S170 to identify groups of forward degenerate primers and corresponding groups of reverse degenerate primers can generate on the order of 100 groups of forward degenerate primers and/or on the order of 100 groups of reverse generate primers; however, variations of the specific example of Block S170 can additionally or alternatively comprise processing the reduced set of candidate degenerate primers according to any other suitable constraints.

While the method of Block S170 above describes selection of the groups of forward degenerate primers prior to selection of the groups of reverse degenerate primers, Block S170 can, however, include selecting reverse primer subsets prior to identification of forward primer subsets corresponding to the reverse primer subsets, or can additionally or alternatively include selecting forward primer subsets and reverse primer subsets concurrently, or in any other suitable order.

1.9 Method—Selection of the Primer Set

Block S180 recites: selecting the primer set, from the set of forward primer-reverse primer subset groups, according to a reaction criterion, which functions to find an ideal subset of forward degenerate primers and a corresponding subset of reverse degenerate primers that can amplify all of the set of target sequences in a specified number of experiments. Similar to Blocks S110-S170, Block S180 is preferably implemented at a computing system specially configured to perform a specialized process during operation, wherein the operation includes a selection operation according to a reaction criterion. As such, Block S180 is preferably implemented using a specialized computing system that is operable in a mode that performs one or more of the operations of Block S180, as described in more detail in Section 2 below.

In particular, in implementation of the method(s) described, amplicons generated allow phylogenetic discrimination of the targets, such that analysis of the amplicons allows for discrimination of targets (e.g., bacteria, yeast, viruses). This is in contrast to methods that generate amplicons of a desired length, but produce amplicons that are otherwise identical to each other and/or similar to each other in a manner that prevents discrimination. As such, Block S180 and/or outputs of the method 100 in general can comprise producing amplicons configured to allow for phylogenetic discrimination of targets.

The reaction criterion in Block S180 is thus configured to maximize the number of experiments that can be performed with the selected primer set, wherein the primer set includes forward and reverse degenerate primers that can amplify all of the target sequences in each experiment. In a specific example, Block S180 can comprise selecting a group of 4-5 forward degenerate primers and a corresponding group of 6-7 reverse degenerate primers can be used to amplify all target sequences of human papilloma viruses that infect humans. Thus, the number of forward degenerate primer types and the number of reverse degenerate primer types may or may not be equal to each other. Block S180 can, however, include selecting the primer set according to any other suitable reaction criteria, based upon the type(s) of experiment(s) being performed. For instance, the primer set can be selected according to any other suitable diagnostic test being performed, in relation to a panel of conditions or a particular condition.

In specific examples, the reaction criterion can be associated with diagnostics associated with at least one or more neurological health conditions, one or more autoimmune condition, one or more endocrine system conditions, one or more mental health conditions, one or more locomotor system conditions, one or more metabolic (associated) disease conditions, one or more cardiovascular disease conditions, one or more cutaneous conditions, one or more sexually transmitted diseases, one or more dental health conditions, one or more gastrointestinal health conditions, and/or any other suitable condition, embodiments, variations, and examples of which are described in U.S. application Ser. No. 14/919,614 filed on 21 Oct. 2015, U.S. application Ser. No. 15/097,862 filed on 13 Apr. 2016, U.S. application Ser. No. 15/098,027 filed on 13 Apr. 2016, U.S. application Ser. No. 15/098,248 filed on 13 Apr. 2016, U.S. application Ser. No. 15/098,236 filed on 13 Apr. 2016, U.S. application Ser. No. 15/098,222 filed on 13 Apr. 2016, U.S. application Ser. No. 15/098,204 filed on 13 Apr. 2016, U.S. application Ser. No. 15/098,174 filed on 13 Apr. 2016, U.S. application Ser. No. 15/098,110 filed on 13 Apr. 2016, U.S. application Ser. No. 15/098,081 filed on 13 Apr. 2016, and U.S. application Ser. No. 15/098,153 filed on 13 Apr. 2016, which are herein incorporated in their entireties by this reference. In these specific examples, Block S180 can include designing and applying primer sets for testing samples, which can facilitate performance of diagnostic tests (e.g., in relation to identifying positive test results, in relation to identifying negative test results), generating of quantitative information (e.g., quantitative parameter values associated with different detected or non-detected targets based on binding behavior), generating of information associated with confidence in different sub-results of the diagnostic test (e.g., confidence ranges, indications of potential false positive results, indications of potential false negative results), generating of information associated with non-conclusive results, and/or generation of any suitable information related to each condition of the disease panel. Additionally or alternatively, with application of the set of selected primers, Block S180 can facilitate generation of information from a sample about health states not associated with diseases.

Figure 1C:
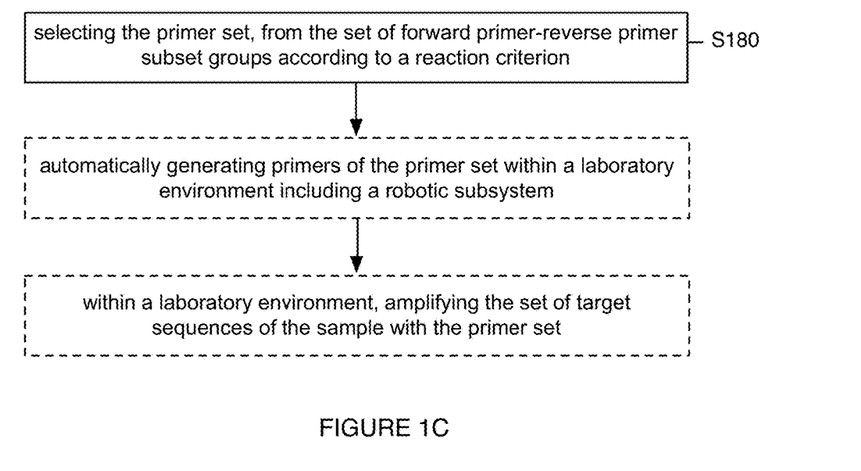
FIG. 1C depicts an example of an additional variation associated with a portion of an embodiment of a method for multiplex primer design.

The method 100 can additionally or alternatively include any other suitable blocks or steps configured to facilitate selection of degenerate primer sets for amplification of a set of target sequences. For instance, as shown in FIG. 1C, some variations of the method 100 can include automatically generating primers of the primer set within a laboratory environment including a robotic subsystem, such that the primer set can be directly applied to amplification of a set of targets of a sample acquired in Block S101 above. In specific examples, the robotic system can be one or more of: a Thermo Fischer Scientific™ robotic lab automation system, an Anton-Paar™ robotic lab automation system, a Transcriptic™ robotic lab automation system, a BioNex™ robotic lab automation system, a Hudson Robotics™ robotic lab automation system, a Biomek® laboratory automation workstation, and any other suitable robotic system that takes primer assembly materials (e.g., bases, oligonucleotide components, buffers, etc.) and assembles primers of the set of primers in solution, with a desired concentration and distribution of different primers of the primer set. However, the method 100 can additionally or alternatively include any other suitable Blocks or Steps configured to design and/or apply a set of primers for amplification and analysis of a set of targets.

2. System

Figure 4A:
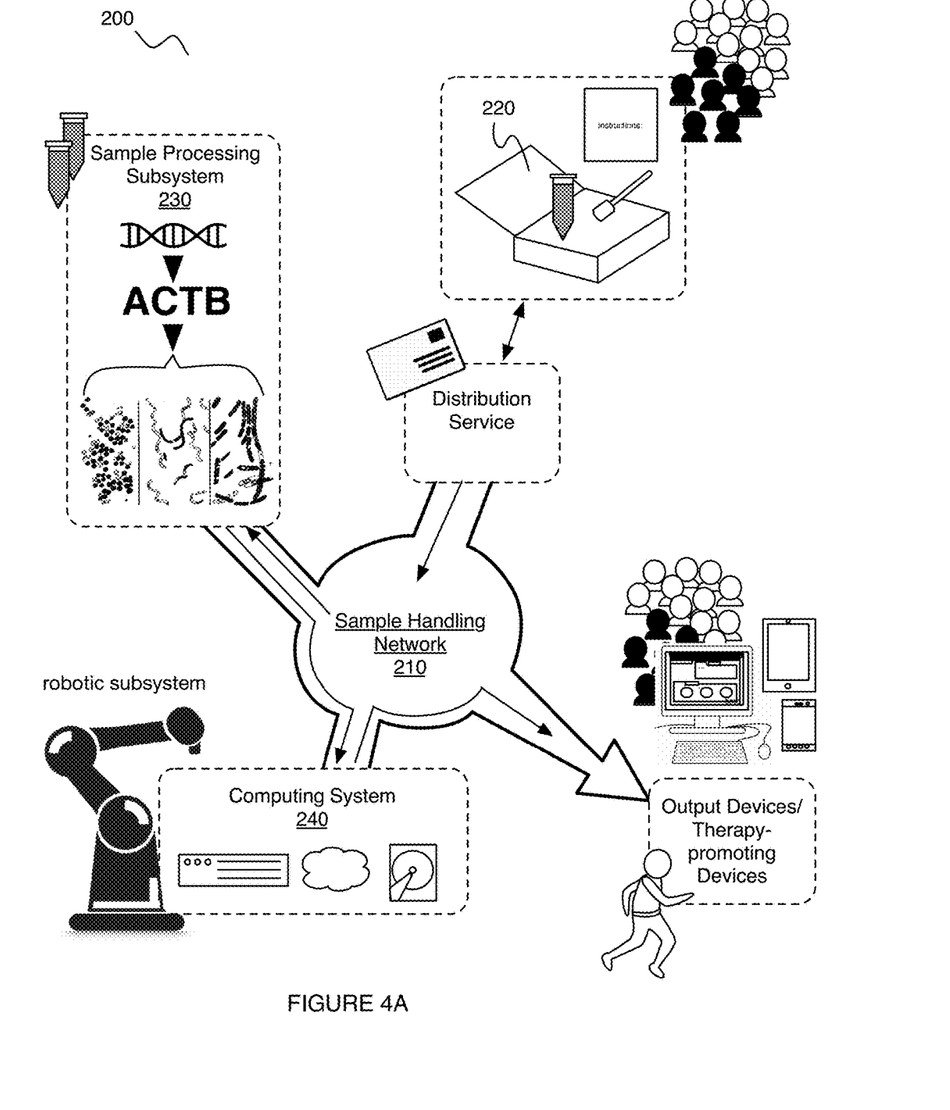
FIGS. 4A-4C depict aspects of embodiments of a system for multiplex primer design.
Figure 4B:
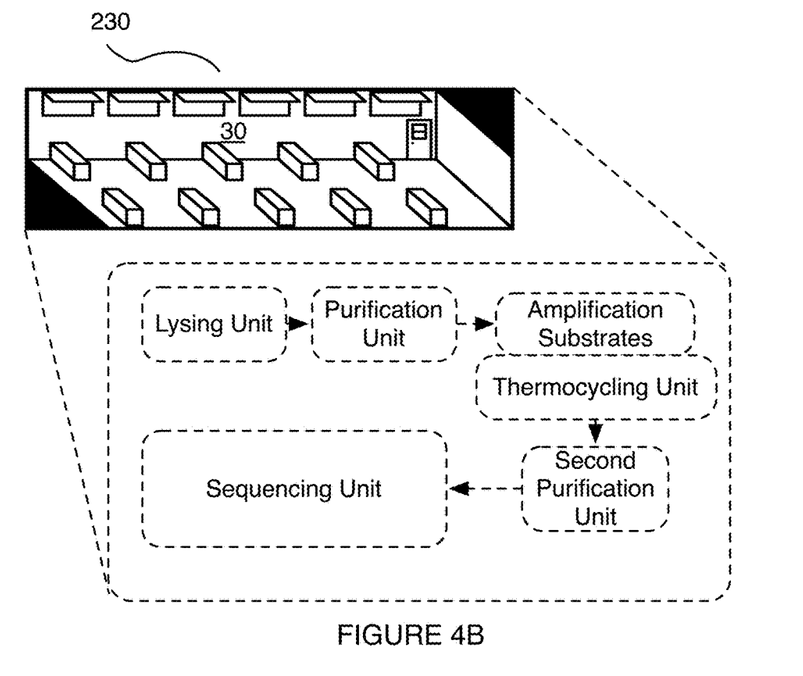
Figure 4C:
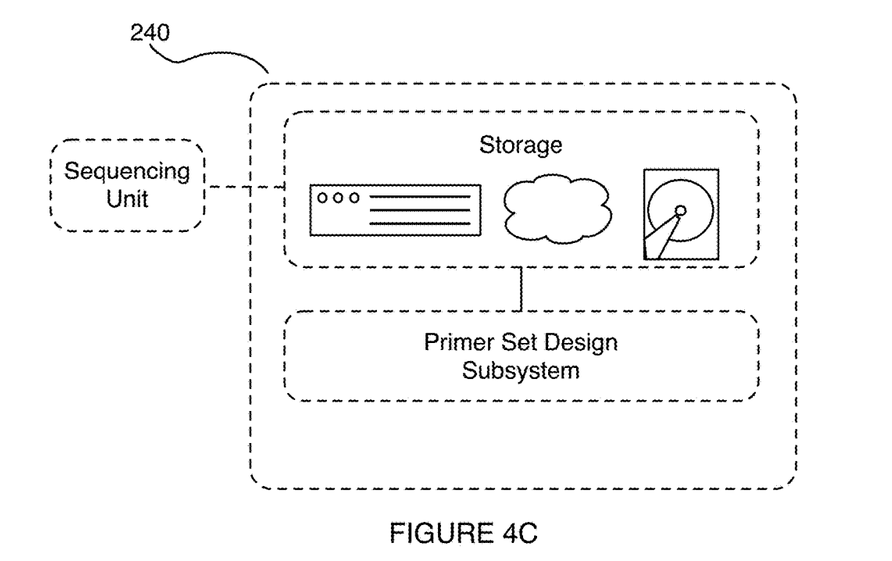

As shown in FIGS. 4A and 4B, a system 200 for selection of a primer set for amplification of a set of target sequences includes: a sample handling network 210 that facilitates: 1) reception of samples from a population of subjects and 2) performs processing of the samples at a sample processing subsystem 230 within the sample handling network based upon a set of primers selected according to an embodiment, variation, or example of the method 100 described in Section 1 above. As such, the system 200 can implement the method 100 above to amplify a set of targets associated with a set of samples simultaneously, in relation to performing diagnostic tests or otherwise characterizing targets present in samples, in an efficient manner.

In variations, the sample handling network of the system 200 can additionally or alternatively 3) perform sequencing operations at a computing system 240 within the sample handling network, and 4) transmit information (e.g., microbiome composition characterizations, microbiome function characterizations, microbial pharmacogenomics information, diagnostic test information, etc.) derived from the sequencing operations to associated entities over communicable links (e.g., secure wireless communication links, secure wired communication links).

In variations, the computing system 240 is thus operable in modes that: 1) identify a set of candidate fragments upon performance of a comparison operation with the set of target sequences; 2) identify a forward subset of unique forward candidates and a reverse subset of unique reverse candidates within the set of candidate fragments; 3) reduce the forward subset and the reverse subset upon performance of a filtering operation, thereby generating a reduced forward subset and a reduced reverse subset that satisfy a set of primer criteria; 4) perform an in silico search operation with the reduced forward subset and the reduced reverse subset, wherein the in silico search operation includes a base mismatch criterion; 5) generate a set of candidate degenerate primers according to outputs of the in silico search operation and the base mismatch criterion; 6) generate a reduced set of candidate degenerate primers upon filtering the set of candidate degenerate primers according to the set of primer criteria; 7) from the reduced set of candidate degenerate primers, select forward primer subsets that amplify the set of target sequences and identifying a reverse primer subset for each of the forward primer subsets with an in silico polymerase chain reaction (PCR) operation, thereby generating a set of forward primer-reverse primer subset groups; and 8) select the primer set, from the set of forward primer-reverse primer subset groups according to a reaction criterion.

As such, the system 200 preferably implements an embodiment, variation, or example of the method 100 described above; however, system 200 can alternatively implement any other suitable method 100 associated with receiving and processing samples, in aggregation with other information, in order to generate and share insights derived from amplifying, sequencing, and analyzing samples in a multiplexed manner.

The sample handling network 210 can functions as a platform from which sampling kits can be distributed in order to receive samples from subjects, wherein the samples can be returned for processing and analysis. One aspect of the sample handling network 210 thus functions as a distribution and receiving hub for sample handling, wherein individuals are able to transmit samples directly to the sample handling network without requiring direct contact between individuals and a clinical or laboratory-based intermediary staffed with trained personnel for biological sample handling. The sample handling network 210 is thus preferably configured to provide instructions directly to individuals pertaining to sample provision in a dependable manner without involving laboratory-trained personnel in the sample provision process, and is preferably configured to associate samples with individuals providing the samples in a secure and reliable manner that is compliant with regulatory standards (e.g., compliant with the Health Insurance Portability and Accountability Act, HIPAA). However, the sample handling network 210 can alternatively be configured to distribute sampling kits and/or receive samples from individuals using a laboratory-based or clinical-based intermediary, and/or handle samples in any other suitable manner.

The sample processing subsystem 230, an example of which is shown in FIG. 7A, is preferably configured to process samples within the sample handling network 210, but can additionally or alternatively be configured to process samples in any other suitable network associated with the sample handling network 210. The sample processing subsystem 230 can comprise a laboratory environment 30 (e.g., wet laboratory environment) within sample handling network 210, wherein samples in sample containers received at the sample handling network 210 are transmitted within the sample handling network 210 to the sample processing subsystem 230 for sample processing (e.g., purification of nucleic acid content, amplification of nucleic acid content, sequencing of nucleic acid content). The sample processing subsystem 230 is preferably implemented entirely within the sample handling network 210, but can additionally or alternatively include sub-modules that are implemented within the sample handling network 210 (e.g., in an "in house" manner) and sub-modules that are implemented outside of the sample handling network 210 (e.g., in an "out of house" manner). In one variation, sample purification can be performed at a first sub-module of the sample processing subsystem 230 within the sample handling network 210, amplification can be performed at a second sub-module of the sample processing subsystem 230 outside of the sample handling network 210, and sequencing can be performed at a third sub-module of the sample processing subsystem 230 outside of the sample handling network 210. The sample processing subsystem 230 and sub-modules thereof can, however, be configured in any other suitable manner in relation to the sample handling network 210.

For sample processing and purification, the sample processing subsystem 230 preferably comprises an environment 30 (e.g., sterilized laboratory hood, sterilized room) sterilized of any contaminating substances (e.g., substances that could affect nucleic acids in a sample or contribute to contaminant nucleic acids), wherein sample processing is conducted. The environment 30 can be temperature controlled, controlled for oxygen content, controlled for carbon dioxide content, and/or controlled for light exposure (e.g., exposure to ultraviolet light). A purification module 232 of the sample processing subsystem 230 can operate based upon force-based separation, sized-based separation, binding-moiety-based separation (e.g., with magnetic binding moieties, with buoyant binding moieties, etc.), and/or any other suitable form of separation. For instance, a purification module 232 can include one or more of: a centrifuge to facilitate extraction of a supernatant, a filter (e.g., a filtration plate), a fluid delivery module configured to combine a lysed sample with moieties that bind to targets and/or waste material of a sample, a wash reagent delivery system, an elution reagent delivery system, and any other suitable apparatus for purification of target content from a sample.

For nucleic acid amplification (e.g., associated with oligonucleotide amplification), the sample processing subsystem 230 can comprise amplification substrates 233 (e.g., PCR-compatible sample-receiving substrates) and a thermocycling module 234 configured to perform thermocycling on the amplification substrates 233, wherein the amplification substrates 233 are configured to receive one or more samples (e.g., lysed samples), primer solutions, reagents (e.g., a master mix, PCR water), and any other suitable materials for nucleic acid amplification. The thermocycling module 234 can be configured to thermocycle different amplification substrates according to individualized thermocycling sequences (e.g., temperatures, ramp up times, hold times, ramp down times, cycles, etc.) using an array of individually controllable heating elements, or can additionally or alternatively be configured to thermocycle different amplification substrates according to common thermocycling sequences using a single heating element or an array of co-controlled heating elements. The sample processing subsystem 230 can additionally or alternatively include a second purification module 235 configured to purify nucleic acid amplification products from amplification reagents (e.g., excess primers, excess dNTPs, enzymes, salts, etc.). In variations, the purification module 235 can include purification kits comprising buffers, alcohols (e.g., ethanol, isopropanol, etc.), pH indicators, chaotropic salts, nucleic acid binding filters, and centrifugation. The sample processing subsystem 230 can, however, comprise any other suitable elements (e.g., spectrophotometric apparatus for quantitation, fluorescence modules for quantitation using fluorescent dyes that bind to nucleic acids, capillary elements for size selection, electrophoretic elements for size selection, filtration elements for size selection, quality control elements, etc.).

For sequencing of amplified nucleic acids, the sample processing subsystem 230 can comprise a sequencing module 236 that operates according to one of: sequencing-by-synthesis techniques (e.g., Illumina sequencing), capillary sequencing techniques (e.g., Sanger sequencing), pyrosequencing techniques, single-molecule real-time (SMRT) techniques, sequencing by ligation (e.g., SOLiD) techniques, reversible terminator sequencing techniques, proton detection sequencing techniques, ion semiconductor (e.g., Ion Torrent) sequencing techniques, nanopore sequencing techniques, electronic sequencing techniques, and any other suitable type of sequencing technique. In specific examples, the sequencing module 236 of the sample processing subsystem 230 can include one or more of: an Applied Biosystems® ABI 3730 DNA Analyzer, a 454 Life Sciences® 454 FLX Titanium sequencer, an Illumina® sequencer (e.g., a GAIIx sequencer, a HiSeq sequencer, a MiSeq sequencer), a Pacific Biosciences® PacBio sequencer, an Ion Torrent™ sequencer, and any other suitable sequencer.

Elements of the sample processing subsystem 230 can be configured to operate in an automated manner, and in one example, the sample processing subsystem 230 comprises a laboratory automation workstation (e.g., a Biomek® Laboratory Automation Workstation) which automates sample container handling and processing by way of robotic arms and gantries, actuators, and fluid delivery systems governed by one or more control modules. Alternatively the sample processing subsystem 230 can be configured to be operated at least in part by a trained technician, in order to provide manual or semi-manual forms of sample handling and processing. Furthermore, the sample processing subsystem 230 can be configured to operate in a continuous-flow manner by using fluidic devices (e.g., microfluidic devices) that enable multiple blocks of processing (e.g., sample lysis, nucleic acid extraction, nucleic acid purification, nucleic acid amplification, etc.) to be performed on a single fluidic device. Alternatively, elements of the sample processing subsystem 230 can be configured to operate more discretely using different devices and/or different sample process chambers.

The computing system 240, an example of which is shown in FIG. 7B, is configured to design an appropriate primer set for simultaneous amplification of a set of targets in sample (in an efficient manner), and/or perform analyses according to blocks of the method 100 described in Section 1 above. The computing system 240 can be in direct communication with modules of the sample processing subsystem 230, and in one variation, a sequencing module 236 of the sample handling network 210 can be configured to provide sequenced data of a set of targets as an output to a module of the computing system 240, after the computing system has selected a primer set and amplified the set of targets with the primer set. Additionally or alternatively, the computing system 240 can be configured to receive inputs from outputs of the sample processing subsystem 230 by way of a storage device 241 configured to store data derived from processing of samples received at the sample handling network 210. The processing system 240 is preferably implemented in one or more computing systems, wherein the computing system(s) can be implemented at least in part in the cloud and/or as a machine (e.g., computing machine, server, cloud-based computing system etc.) configured to receive a computer-readable medium storing computer-readable instructions. As such, the computing system 240 can comprise one or more processing modules, implemented in the cloud and/or as machine, comprising instructions for performing blocks of the method 100. The computing system 240 can, however, be configured in any other suitable manner.

In relation to automated generation and/or application of the set of primers to amplification of targets in a sample, the system 200 can comprise a robotic subsystem within the laboratory environment, wherein the robotic subsystem is in communication with the computing system 240. In variations, the robotic subsystem can include liquid handling apparatus in communication with reservoirs of process fluids, in addition to arms and actuators (e.g., gantries, motors, etc.) configured to drive movement of one or more of the liquid handling apparatus and arms to facilitate primer assembly. In specific examples, the robotic subsystem can include one or more of: a Thermo Fischer Scientific™ robotic lab automation system, an Anton-Paar™ robotic lab automation system, a Transcriptic™ robotic lab automation system, a BioNex™ robotic lab automation system, a Hudson Robotics™ robotic lab automation system, a Biomek® laboratory automation workstation, and any other suitable robotic system that takes primer assembly materials (e.g., bases, oligonucleotide components, buffers, etc.) and assembles primers of the set of primers in solution, with a desired concentration and distribution of different primers of the primer set. However, the system 200 can additionally or alternatively include any other suitable elements configured to design and/or apply a set of primers for amplification and analysis of a set of targets.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for selection of a primer set for simultaneous amplification of a set of nucleic acid target sequences, comprising:
   receiving a biological sample comprising the set of nucleic acid target sequences associated with a set of different targets;
   at a computing system, identifying a set of candidate fragments upon performance of a comparison operation with the set of nucleic acid target sequences;
   within the set of candidate fragments, identifying a forward subset of unique forward candidates and a reverse subset of unique reverse candidates;
   at the computing system, reducing the forward subset of unique forward candidates and the reverse subset of unique reverse candidates upon performance of a filtering operation, thereby generating a reduced forward subset and a reduced reverse subset that satisfy a set of primer criteria;
   at the computing system, with the reduced forward subset and the reduced reverse subset, performing an in silico search operation, wherein the in silico search operation includes a base mismatch criterion;
   at the computing system, according to outputs of the in silico search operation and the base mismatch criterion, generating a set of candidate degenerate primers;
   at the computing system, generating a reduced set of candidate degenerate primers upon filtering the set of candidate degenerate primers according to the set of primer criteria;
   from the reduced set of candidate degenerate primers, selecting forward primer subsets that amplify the set of nucleic acid target sequences and identifying a reverse primer subset for each of the forward primer subsets with an in silico polymerase chain reaction (PCR) operation, thereby generating a set of forward primer-reverse primer subset groups;
   at the computing system, from the set of forward primer-reverse primer subset groups, selecting the primer set according to a reaction criterion; and
   within a laboratory environment, amplifying, with the primer set, the set of nucleic acid target sequences of the biological sample.

2. The method of claim 1, wherein identifying the set of candidate fragments using at least one of: a basic local alignment search tool (BLAST) with the set of nucleic acid target sequences and any other suitable bioinformatics tools for sequence alignment, wherein the set of candidate fragments have a word size parameter from 17-40 characters in length.

3. The method of claim 1, wherein identifying the forward subset of unique forward candidates and the reverse subset of unique reverse candidates within the set of candidate fragments comprises identifying at least one candidate of the set of candidate fragments that are unique in primer sequence position, and wherein the forward subset and the reverse subset comprise a distribution of fragment lengths.

4. The method of claim 1, wherein reducing the forward subset of unique forward candidates and the reverse subset of unique reverse candidates upon performance of the filtering operation comprises performing the filtering operation with a set of criteria including at least one of: a GC clamp criterion, a GC content criterion, a run criterion, a dinucleotide-associated criterion, a binding energy criterion, and a primer dimer criterion.

5. The method of claim 4, wherein performing the filtering operation comprises implementing at least one of a first criterion associated with limiting a tendency to form primer dimers, and a second criterion associated with limiting shortening of resultant amplicon products.

6. The method of claim 4, wherein performing the filtering operation includes ranking each candidate fragment of the forward subset and the reverse subset according to a weighted summation of criterion values of the set of criteria of each of the forward subset and the reverse subset.

7. The method of claim 1, wherein the base mismatch criterion of the in silico search operation comprises a mismatch criterion of up to 3 mismatches for each of the reduced forward subset and the reduced reverse subset.

8. The method of claim 7, wherein, in relation to the mismatch criterion, each of the reduced forward subset and the reduced reverse subset includes mismatches in at least one of different bases and different positions.

9. The method of claim 1, further comprising automatically generating at least one primer of the primer set within the laboratory environment, wherein generating the at least one primer includes assembling the at least one primer of the primer set with a robotic subsystem.

10. The method of claim 9, further comprising generating an analysis of the set of nucleic acid target sequences upon amplification with the primer set, wherein the analysis provides a diagnostic assessment of the biological sample for at least one condition from a panel including different health conditions.

11. The method of claim 1, further comprising: upon amplifying the set of nucleic acid target sequences, producing amplicons configured to allow for phylogenetic discrimination of targets associated with the set of nucleic acid target sequences.

12. The method of claim 1, wherein identifying the set of candidate fragments comprises: selecting a desired fragment length, and fragmenting all targets into target fragments having the desired fragment length, the method further including identifying a most common fragment amongst the target fragments.

13. A method for selection of a primer set for simultaneous amplification of a set of nucleic acid target sequences, comprising:
at a computing system, identifying a set of candidate fragments upon performance of a comparison operation with the set of nucleic acid target sequences;
identifying a forward subset of unique forward candidates and a reverse subset of unique reverse candidates within the set of candidate fragments;
at the computing system, reducing the forward subset of unique forward candidates and the reverse subset of unique reverse candidates upon performance of a filtering operation, thereby generating a reduced forward subset and a reduced reverse subset that satisfy a set of primer criteria;
at the computing system, performing an in silico search operation with the reduced forward subset and the reduced reverse subset;
at the computing system, generating a set of candidate degenerate primers according to outputs of the in silico search operation;
at the computing system, generating a reduced set of candidate degenerate primers upon filtering the set of candidate degenerate primers according to the set of primer criteria;
from the reduced set of candidate degenerate primers, selecting forward primer subsets that amplify the set of nucleic acid target sequences and identifying a reverse primer subset for each of the forward primer subsets, thereby generating a set of forward primer-reverse primer subset groups;
at the computing system, selecting the primer set, from the set of forward primer-reverse primer subset groups according to a reaction criterion; and
within a laboratory environment, amplifying the set of nucleic acid target sequences of a biological sample with the primer set.

14. The method of claim 13, further comprising receiving the biological sample having a set of different targets associated with the set of nucleic acid target sequences, and within the laboratory environment, amplifying the set of nucleic acid target sequences of the biological sample with the primer set.

15. The method of claim 13, wherein identifying the set of candidate fragments using at least one of: a basic local alignment search tool (BLAST) with the set of nucleic acid target sequences and any other suitable bioinformatics tools for sequence alignment, wherein the set of candidate fragments have a word size parameter from at least 12-45 characters in length.

16. The method of claim 15, wherein identifying the forward subset of unique forward candidates and the reverse subset of unique reverse candidates within the set of candidate fragments comprises identifying at least one candidate of the set of candidate fragments that are close in primer sequence position, and wherein the forward subset and the reverse subset comprise a distribution of fragment lengths.

17. The method of claim 16, wherein performing the in silico search operation comprises performing the in silico search operation with a base mismatch criterion of up to 5 mismatches for each of the reduced forward subset and the reduced reverse subset.

18. The method of claim 13, wherein performance of the filtering operation includes ranking each candidate fragment of the forward subset of unique forward candidates and the reverse subset of unique reverse candidates according to a weighted summation of criterion values of the set of criteria of each of the forward subset of unique forward candidates and the reverse subset of unique reverse candidates.

19. The method of claim 13, wherein performing the in silico search operation comprises performing the in silico search operation with at least one of: a Hamming distance threshold and another in silico operation.

20. The method of claim 13, further comprising generating an analysis of the set of nucleic acid target sequences upon amplification with the primer set, wherein the analysis provides a diagnostic assessment associated with the biological sample for at least one condition from a panel including different health conditions.

21. The method of claim 20, wherein the panel including different health conditions includes at least one specific condition from a panel of sexually-transmitted diseases.

22. The method of claim 13, further comprising generating an analysis of the set of nucleic acid target sequences upon amplification with the primer set, wherein the analysis provides a characteristic assessment of at least one of: a microbiome composition of the biological sample, a set of microbiome functional features of the biological sample, a set of taxonomic features of the biological sample and a set of pharmacogenomic features of the biological sample.

23. The method of claim 13, further comprising automatically generating at least one primer of the primer set within the laboratory environment, wherein generating the at least one primer includes assembling the at least one primer of the primer set with a robotic subsystem.

* * * * *